(12) United States Patent
Takahashi (10) Patent No.: US 12,067,672 B2
(45) Date of Patent: Aug. 20, 2024

(54) ENDOSCOPIC IMAGE PROCESSING APPARATUS, ENDOSCOPE SYSTEM, AND METHOD OF OPERATING ENDOSCOPIC IMAGE PROCESSING APPARATUS

(71) Applicant: EVIIDENT CORPORATION, Nagano (JP)

(72) Inventor: Hideaki Takahashi, Musashimurayama (JP)

(73) Assignee: Evident Corporation, Nagano (JP)

( * ) Notice: Subject to any disclaimer, the term of this patent is extended or adjusted under 35 U.S.C. 154(b) by 281 days.

(21) Appl. No.: 17/513,353

(22) Filed: Oct. 28, 2021

(65) Prior Publication Data

US 2022/0051472 A1    Feb. 17, 2022

Related U.S. Application Data

(63) Continuation of application No. PCT/JP2019/046545, filed on Nov. 28, 2019.

(51) Int. Cl.
*H04N 13/221* (2018.01)
*G06T 7/20* (2017.01)
*G06T 15/20* (2011.01)

(52) U.S. Cl.
CPC ............ *G06T 15/205* (2013.01); *G06T 7/20* (2013.01); *H04N 13/221* (2018.05); *G06T 2207/10068* (2013.01)

(58) Field of Classification Search
CPC ............ G06T 15/205; G06T 7/20; G06T 2207/10068; H04N 13/221; A61B 1/00194
See application file for complete search history.

(56) References Cited

U.S. PATENT DOCUMENTS

2005/0251017 A1* 11/2005 Azar ................ A61B 5/06
                                                    600/407
2007/0161853 A1   7/2007 Yagi et al.
(Continued)

FOREIGN PATENT DOCUMENTS

JP    2004-049638 A    2/2004
JP    2006-255440 A    9/2006
(Continued)

OTHER PUBLICATIONS

International Search Report dated Mar. 3, 2020 received in PCT/JP2019/046545.

*Primary Examiner* — Kyle M Lotfi
(74) *Attorney, Agent, or Firm* — Scully, Scott, Murphy & Presser, P.C.

(57) ABSTRACT

An endoscopic image processing apparatus is configured to create a three-dimensional shape model of an object by performing processing on an endoscopic image group of an inside of the object, and includes a processor. The processor estimates a self-position of the image pickup device based on the endoscopic image group, calculates a first displacement amount corresponding to a displacement amount of the image pickup device based on an estimation result of the self-position of the image pickup device obtained by the estimation, calculates a second displacement amount corresponding to a displacement amount in a direction parallel to a longitudinal axis direction of the insertion portion, based on a detection signal outputted from an insertion/removal state detection device that detects an insertion/removal state of an insertion portion inserted into the object, and generates scale information in which the first displacement amount and the second displacement amount are associated with each other.

18 Claims, 8 Drawing Sheets

(56) References Cited

U.S. PATENT DOCUMENTS

| | | |
|---|---|---|
| 2011/0242301 A1 | 10/2011 | Morita |
| 2015/0182144 A1 | 7/2015 | Bharat et al. |
| 2015/0341600 A1 | 11/2015 | Hatcher, Jr. et al. |
| 2017/0347916 A1 | 12/2017 | Hane et al. |
| 2019/0082933 A1 | 3/2019 | Takahashi et al. |

FOREIGN PATENT DOCUMENTS

| | | |
|---|---|---|
| JP | 2007-283115 A | 11/2007 |
| JP | 4631057 B2 | 2/2011 |
| JP | 2011-206251 A | 10/2011 |
| JP | 2015-529494 A | 10/2015 |
| JP | 2017-129904 A | 7/2017 |
| WO | 2005/077253 A1 | 8/2005 |
| WO | 2014/024069 A1 | 2/2014 |
| WO | 2015/179057 A1 | 11/2015 |
| WO | 2016/135966 A1 | 9/2016 |
| WO | 2017/057330 A1 | 4/2017 |
| WO | 2017/221298 A1 | 12/2017 |

* cited by examiner

ENDOSCOPIC IMAGE PROCESSING APPARATUS, ENDOSCOPE SYSTEM, AND METHOD OF OPERATING ENDOSCOPIC IMAGE PROCESSING APPARATUS

CROSS REFERENCE TO RELATED APPLICATION

This application is a continuation application of PCT/JP2019/046545 filed on Nov. 28, 2019, the entire contents of which are incorporated herein by this reference.

BACKGROUND OF THE INVENTION

1. Field of the Invention

The present invention relates to an endoscopic image processing apparatus, an endoscope system, and a method of operating an endoscopic image processing apparatus.

2. Description of the Related Art

An endoscopic inspection in an industrial field has been used as a method to nondestructively inspect an object such as a turbine and an engine. Further, in the endoscopic inspection in the industrial field, for example, adoption of a method of visual simultaneous localization and mapping (SLAM) has been examined in recent years as a method to obtain information useful for the inspection of the object, such as a size of a defective portion present inside the object, while eliminating physical components (motion sensor, etc.) used for distance measurement or attitude detection from an endoscope as much as possible. For example, Japanese Patent Application Laid-Open Publication No. 2017-129904 discloses a viewpoint to estimate a size of an object present in a real space by applying the method of visual SLAM (hereinafter, also referred to as VSLAM) to an image obtained by picking up an image of the object.

In a case where the method of VSLAM is used in the endoscopic inspection in the industrial field, for example, information corresponding to a relative positional relationship between an object present in a real space and an image pickup unit provided in an endoscope inserted into the object is acquired, and a three-dimensional shape of the object is sequentially reconstructed based on the acquired information.

SUMMARY OF THE INVENTION

An endoscopic image processing apparatus according to an aspect of the present invention is an endoscopic image processing apparatus configured to create a three-dimensional shape model of an object by performing processing on an endoscopic image group obtained by causing an image pickup device provided at a distal end portion of an elongated insertion portion to pick up images of an inside of the object. The endoscopic image processing apparatus includes a processor. The processor estimates a self-position of the image pickup device based on the endoscopic image group, calculates a first displacement amount corresponding to a displacement amount of the image pickup device based on an estimation result of the self-position of the image pickup device obtained by the estimation, calculates a second displacement amount corresponding to a displacement amount in a direction parallel to a longitudinal axis direction of the insertion portion, based on a detection signal outputted from an insertion/removal state detection device that detects an insertion/removal state of the insertion portion inserted into the object, and generates scale information in which the first displacement amount and the second displacement amount are associated with each other, as information used for processing relating to creation of the three-dimensional shape model of the object.

An endoscope system according to another aspect of the present invention includes: an endoscope configured to cause an image pickup device provided at a distal end portion of an elongated insertion portion to pick up images of an inside of an object; an insertion/removal state detection device configured to detect an insertion/removal state of the insertion portion inserted into the object and to output a detection signal; and a processor. The processor estimates a self-position of the image pickup device based on an endoscopic image group obtained by picking up images of the inside of the object by the endoscope, calculates a first displacement amount corresponding to a displacement amount of the image pickup device based on an estimation result of the self-position of the image pickup device obtained by the estimation, calculates a second displacement amount corresponding to a displacement amount in a direction parallel to a longitudinal axis direction of the insertion portion, based on the detection signal outputted from the insertion/removal state detection device, and generates scale information in which the first displacement amount and the second displacement amount are associated with each other, as information used for processing relating to creation of a three-dimensional shape model of the object.

A method of operating an endoscopic image processing apparatus according to yet another aspect of the present invention is a method of operating an endoscopic image processing apparatus configured to create a three-dimensional shape model of an object by performing processing on an endoscopic image group obtained by causing an image pickup device provided at a distal end portion of an elongated insertion portion to pick up images of an inside of the object. The method includes: estimating a self-position of the image pickup device based on the endoscopic image group; calculating a first displacement amount corresponding to a displacement amount of the image pickup device based on an estimation result of the self-position of the image pickup device obtained by the estimation; calculating a second displacement amount corresponding to a displacement amount in a direction parallel to a longitudinal axis direction of the insertion portion, based on a detection signal outputted from an insertion/removal state detection device that detects an insertion/removal state of the insertion portion inserted into the object; and generating scale information in which the first displacement amount and the second displacement amount are associated with each other, as information used for processing relating to creation of the three-dimensional shape model of the object.

DETAILED DESCRIPTION OF THE PREFERRED EMBODIMENT

An embodiment of the present invention is described below with reference to drawings.

Figure 1:
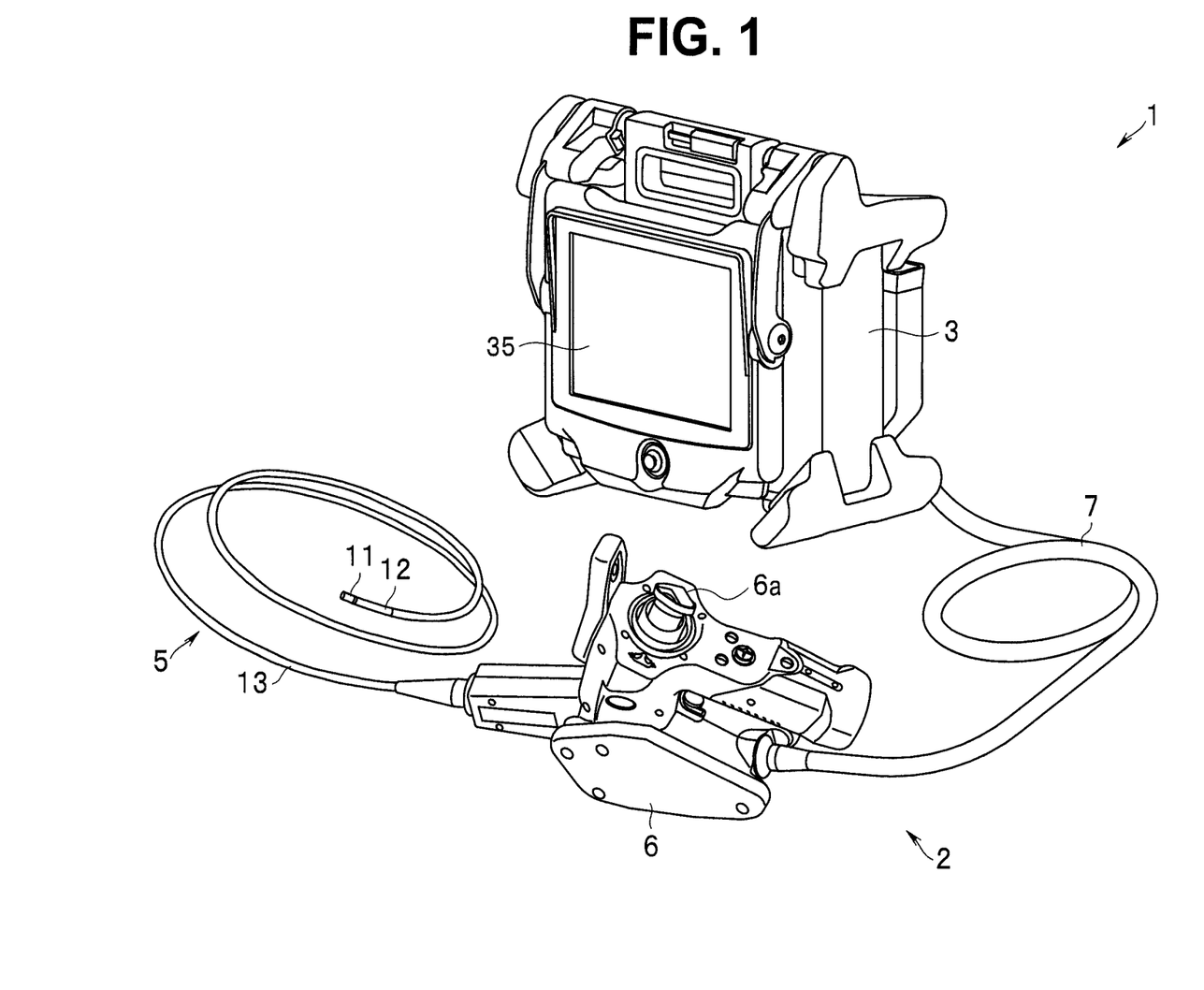
FIG. 1 is a diagram illustrating an example of an appearance configuration of an endoscope system including an endoscopic image processing apparatus according to an embodiment.

For example, as illustrated in FIG. 1, an endoscope system 1 includes an endoscope 2 and a main body apparatus 3 to which the endoscope 2 is connectable. The main body apparatus 3 includes a display unit 35 that can display an image and the like. FIG. 1 is a diagram illustrating an example of an appearance configuration of the endoscope system including an endoscopic image processing apparatus according to the embodiment.

The endoscope 2 includes an insertion portion 5, an operation portion 6, and a universal cord 7. The insertion portion 5 is formed in an elongated shape insertable into an object such as a turbine and an engine. The operation portion 6 is provided on a proximal end side of the insertion portion 5. The universal cord 7 extends from the operation portion 6. Further, the endoscope 2 is configured so as to be removably connected to the main body apparatus 3 by the universal cord 7.

The insertion portion 5 includes a distal end portion 11, a bendably-formed bending portion 12, and a long flexible tube portion 13 having flexibility in order from a distal end side.

The operation portion 6 includes a bending operator 6a including a joystick that enables operation to bend the bending portion 12 in a desired direction. Although not illustrated, the operation portion 6 further includes one or more operation buttons corresponding to functions usable in the endoscope system 1, such as a freeze button, a bending lock button, and a recording instruction button.

Figure 2:
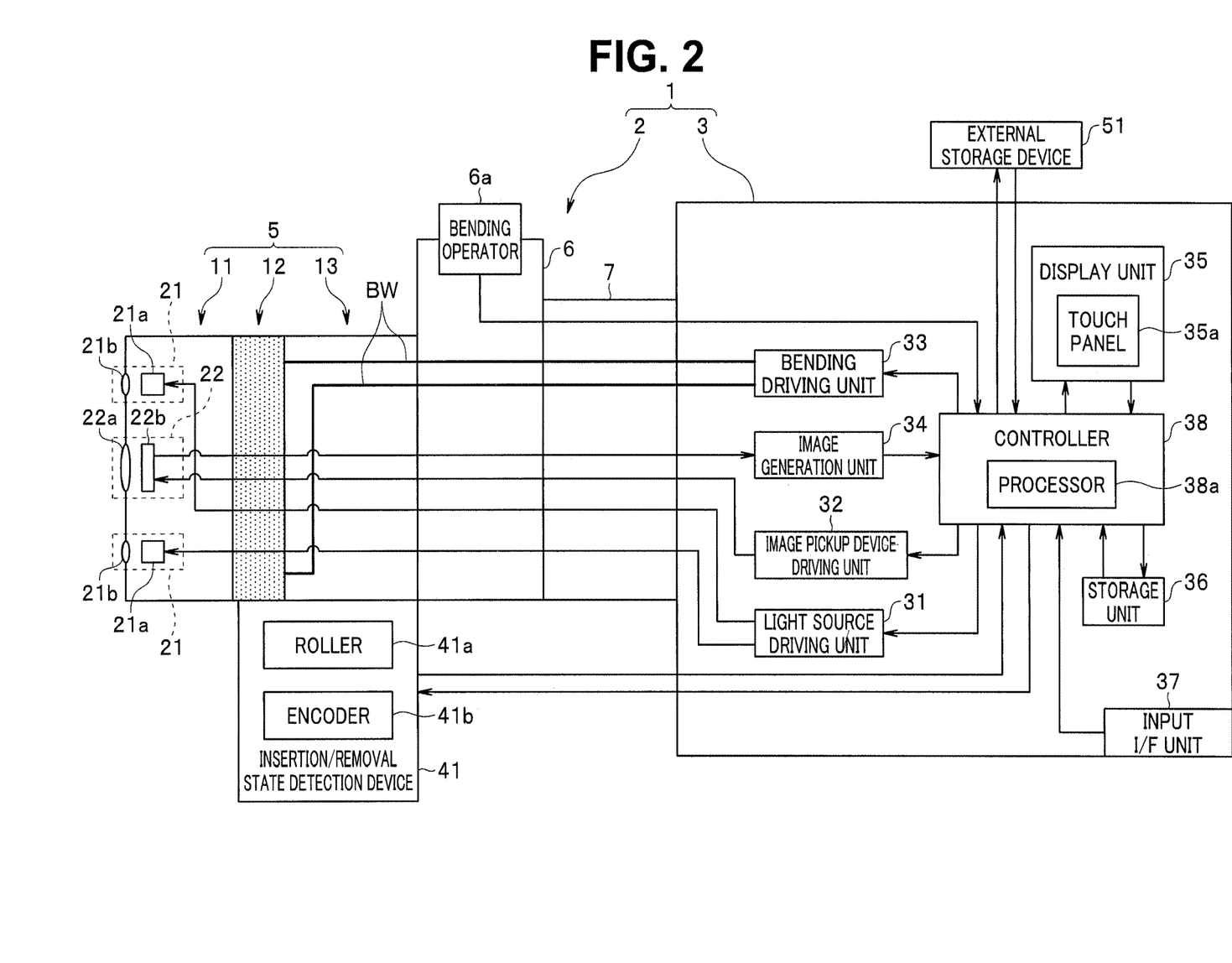
FIG. 2 is a block diagram to explain a configuration of the endoscope system including the endoscopic image processing apparatus according to the embodiment.

As illustrated in FIG. 2, the distal end portion 11 includes one or more light source units 21 and an image pickup unit 22. In FIG. 2, a case where two light source units 21 are provided in the distal end portion 11 is illustrated for convenience of illustration. FIG. 2 is a block diagram to explain a configuration of the endoscope system including the endoscopic image processing apparatus according to the embodiment.

Each of the light source units 21 includes a light emitting element 21a and an illumination optical system 21b.

Each of the light emitting elements 21a includes, for example, an LED. Each of the light emitting elements 21a generates illumination light having a light quantity corresponding to a light emitting element driving signal supplied from the main body apparatus 3.

Each of the illumination optical systems 21b is configured as an optical system including, for example, an illumination lens. Further, each of the illumination optical systems 21b applies illumination light emitted from the corresponding light emitting element 21a to an image pickup object outside the distal end portion 11.

The image pickup unit 22 is configured as a camera including an observation optical system 22a and an image pickup device 22b.

The observation optical system 22a is configured as an optical system including, for example, an imaging lens. Further, the observation optical system 22a receives return light (reflected light) emitted from the image pickup object outside the distal end portion 11 due to application of the illumination light from the light source units 21, and forms an image of the return light on an image pickup plane of the image pickup device 22b.

The image pickup device 22b, for example, an imaging device, includes an image sensor such as a CCD and a CMOS. Further, the image pickup device 22b is driven in response to an image pickup device driving signal supplied from the main body apparatus 3. The image pickup device 22b generates an image pickup signal by picking up an image of the return light imaged by the observation optical system 22a and outputs the generated image pickup signal to the main body apparatus 3.

The bending portion 12 includes, for example, a plurality of bending pieces. The bending portion 12 is connected to a distal end portion of each of a plurality of bending wires BW inserted into the flexible tube portion 13, the operation portion 6, and the universal cord 7. Further, the bending portion 12 can direct the distal end portion 11 to a direction intersecting a longitudinal axis direction of the insertion portion 5 by bending based on a traction state of each of the plurality of bending wires BW.

In other words, the endoscope 2 picks up an image of an inside of the object by the image pickup unit 22 provided at the distal end portion 11 of the elongated insertion portion 5.

As illustrated in FIG. 2, the main body apparatus 3 includes a light source driving unit 31, an image pickup device driving unit 32, a bending driving unit 33, an image generation unit 34, a display unit 35, a storage unit 36, an input I/F (interface) unit 37, and a controller 38. The main body apparatus 3 further includes a connection port (not illustrated) for connection of a portable external storage device 51 such as a USB memory.

The light source driving unit 31 includes, for example, a light source driving circuit. Further, the light source driving unit 31 generates and outputs the light emitting element driving signal to drive the light emitting elements 21a under the control of the controller 38.

The image pickup device driving unit 32 includes, for example, an image pickup device driving circuit. Further, the image pickup device driving unit 32 generates and outputs the image pickup device driving signal to drive the image pickup device 22b under the control of the controller 38.

The bending driving unit 33 includes, for example, a motor. The bending driving unit 33 is connected to a proximal end portion of each of the plurality of bending wires BW. Further, the bending driving unit 33 can individually change traction quantities of the plurality of bending wires BW under the control of the controller 38. In other words, the bending driving unit 33 can change a traction state of each of the plurality of bending wires BW under the control of the controller 38.

The image generation unit 34 includes an integrated circuit such as an FPGA (field programmable gate array). Further, the image generation unit 34 generates endoscopic images by performing predetermined signal processing on the image pickup signal outputted from the image pickup device 22b, and sequentially outputs the generated endoscopic images to the controller 38.

The display unit 35 includes, for example, a liquid crystal panel. The display unit 35 displays a display image outputted from the controller 38 on a display screen. Further, the display unit 35 includes a touch panel 35a that detects touch operation to GUI (graphical user interface) buttons and the like displayed on the display screen and issues an instruction corresponding to the detected touch operation to the controller 38.

The storage unit 36 includes a storage medium such as a memory. The storage unit 36 stores various programs corresponding to operation of the controller 38, for example, programs used for control of the units of the endoscope system 1 and programs to perform processing relating to VSLAM described below. Further, the storage unit 36 can store the endoscopic images and the like used for the processing relating to VSLAM by the controller 38.

The input I/F unit 37 includes switches or the like that can issue instructions corresponding to input operation of a user, to the controller 38.

The controller 38 includes one or more processors 38a such as CPUs. The controller 38 can control the light source driving unit 31 and the image pickup device driving unit 32 based on an instruction issued in response to operation of the touch panel 35a or the input I/F unit 37. The controller 38 can control the bending driving unit 33 to bend the bending portion 12 based on an instruction issued in response to operation of the bending operator 6a. The controller 38 can generate a display image in which the GUI buttons and the like are superimposed on the endoscopic images and the like outputted from the image generation unit 34, and can output the display image to the display unit 35. The controller 38 can generate a display image that includes the endoscopic images outputted from the image generation unit 34 and a three-dimensional shape model of the object created by the processing relating to VSLAM described below, and can output the display image to the display unit 35. The controller 38 can encode the endoscopic images outputted from the image generation unit 34 by using a format for a still image such as a JPEG and a format for a movie such as MPEG4, and can store the encoded endoscopic images in the external storage device 51. The controller 38 can read the image stored in the external storage device 51 based on an instruction issued in response to operation of the touch panel 35a or the input I/F unit 37, and can generate a display image corresponding to the read image and output the display image to the display unit 35. The controller 38 performs predetermined image processing such as color space conversion, interlace/progressive conversion, and gamma correction, on the display image to be outputted to the display unit 35.

The controller 38 generates a synchronization signal to synchronize operation of the image pickup unit 22 and operation of an insertion/removal state detection device 41, and outputs the generated synchronization signal to the image pickup device driving unit 32 and the insertion/removal state detection device 41. The controller 38 outputs the above-described synchronization signal and performs the processing relating to VSLAM based on an endoscopic image group including the plurality of endoscopic images sequentially outputted from the image generation unit 34, and a detection signal outputted from the insertion/removal state detection device 41.

Note that, in the present embodiment, description is given by assuming that the processing relating to VSLAM at least includes, for example, processing to extract a plurality of feature points (corresponding points) matching in the endoscopic image group outputted from the image generation unit 34, processing to estimate a self-position of the image pickup unit 22 corresponding to the plurality of feature points and to acquire a result of the estimation, and processing to create the three-dimensional shape model of the object corresponding to the plurality of feature points and the result of the estimation as an environment map. Specific examples of the processing performed by the controller 38 are described below.

In the present embodiment, the processors 38a may perform processing, operation, and the like similar to the processing, the operation, and the like of the controller 38 by executing programs read from the storage unit 36. Further, in the present embodiment, the controller 38 may include a processor including an integrated circuit such as an FPGA, in place of the processors 38a such as CPUs.

In other words, the main body apparatus 3 includes a function as the endoscopic image processing apparatus, and performs processing on the endoscopic image group that is obtained by picking up images of the inside of the object by the image pickup unit 22 provided at the distal end portion 11 of the insertion portion 5, to create the three-dimensional shape model of the object.

In the present embodiment, in inspection of the object by using the endoscope 2, the insertion/removal state detection device 41 that can detect an insertion/removal state of the insertion portion 5 is used together.

The insertion/removal state detection device 41 can transmit and receive signals and the like to/from the main body apparatus 3. The insertion/removal state detection device 41 detects the insertion/removal state of the insertion portion 5 inserted into the object, and generates the detection signal representing the detected insertion/removal state of the insertion portion 5 and outputs the detection signal to the main body apparatus 3. The insertion/removal state detection device 41 includes, for example, a through hole (not illustrated) formed in a shape that can displace the insertion portion 5 in the longitudinal axis direction while the insertion portion 5 is inserted into the through hole. The insertion/removal state detection device 41 includes a roller 41a and an encoder 41b.

The roller 41a is provided at, for example, a predetermined position inside the through hole of the insertion/removal state detection device 41. Further, the roller 41a rotates in a rotation direction corresponding to a displacement direction of the insertion portion 5 and rotates by a rotation amount corresponding to a displacement amount of the insertion portion 5 while being in contact with an outer surface of the insertion portion 5 inserted into the through hole of the insertion/removal state detection device 41.

The encoder 41b generates the detection signal having a waveform corresponding to the rotation direction and the rotation amount of the roller 41a and outputs the detection signal to the main body apparatus 3 at a timing set by the synchronization signal outputted from the controller 38.

More specifically, at the timing set by the synchronization signal outputted from the controller 38, the encoder 41b generates, for example, two types of pulse signals corresponding to two phases of an A-phase and a B-phase, and outputs the two types of generated pulse signals as the detection signal to the main body apparatus 3.

The insertion/removal state detection device 41 including the above-described configuration can output, to the main body apparatus 3, the detection signal having waveforms different between a case where the insertion portion 5 inserted into the object is advanced and a case where the insertion portion 5 inserted into the object is retracted. Further, the insertion/removal state detection device 41 including the above-described configuration can output, to the main body apparatus 3, the detection signal having the waveforms different based on the displacement amount when the insertion portion 5 inserted into the object is displaced. In other words, the insertion/removal state detection device 41 including the above-described configuration can detect, as the insertion/removal state of the insertion portion 5 inserted into the object, the displacement amount and the displacement direction of the insertion portion 5 in the longitudinal axis direction.

Subsequently, action of the present embodiment is described. Note that, in the following, description is given by assuming that inspection is performed while the insertion portion 5 is inserted into a tube-shaped object such as a conduit.

Before an object inspection using the endoscope 2, the user fixes the insertion/removal state detection device 41 at a predetermined position near an insertion port for insertion of the insertion portion 5 into the object.

According to the present embodiment, it is sufficient to dispose the insertion/removal state detection device 41 at a position where a relative position to the object into which the insertion portion 5 is inserted is not changed. Therefore, according to the present embodiment, for example, the insertion/removal state detection device 41 may be fixed at a position separated from the above-described insertion port.

After the user turns on the units of the endoscope system 1, the user brings the distal end portion 11 to a desired site inside the object by performing insertion operation to insert the insertion portion 5 into the object. In response to such user operation, the illumination light emitted from the light emitting elements 21a is applied to an image pickup object inside the object, the image pickup signal generated by picking up an image of reflected light from the image pickup object is outputted from the image pickup device 22b, and endoscopic images generated based on the image pickup signal are sequentially outputted from the image generation unit 34 to the controller 38. Further, after the user brings the distal end portion 11 to the desired site inside the object, the user performs removal operation to remove the insertion portion 5 from the inside of the object.

Figure 3:
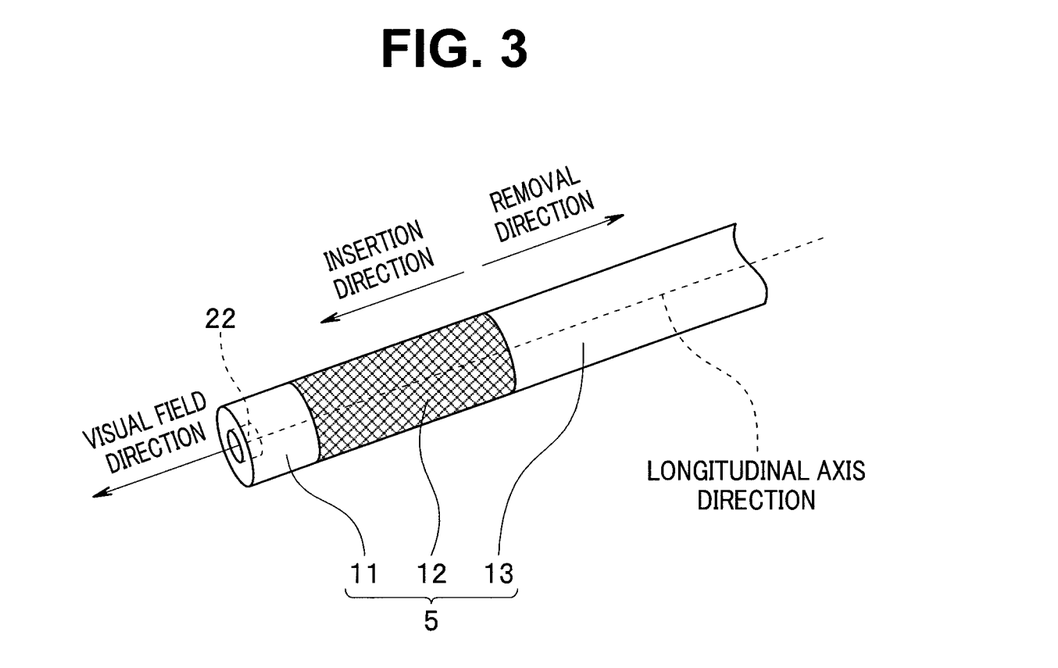
FIG. 3 is a diagram to explain a relationship between a visual field direction of an image pickup unit and both of an insertion direction and a removal direction of an insertion portion.

According to the above-described insertion operation by the user, it is possible to make a visual field direction of the image pickup unit 22 corresponding to a front side of the distal end portion 11 coincident with an insertion direction (see FIG. 3) corresponding to a direction from the proximal end side toward the distal end side of the insertion portion 5 in the longitudinal axis direction of the insertion portion 5. Further, according to the above-described removal operation by the user, it is possible to make the visual field direction of the image pickup unit 22 coincident with a removal direction (see FIG. 3) corresponding to a direction from the distal end side toward the proximal end side of the insertion portion 5 in the longitudinal axis direction of the insertion portion 5. FIG. 3 is a diagram to explain a relationship between the visual field direction of the image pickup unit and both of the insertion direction and the removal direction of the insertion portion.

When detecting a state where the signals and the like are transmittable and receivable between the main body apparatus 3 and the insertion/removal state detection device 41, the controller 38 generates the synchronization signal to synchronize the operation of the image pickup unit 22 and the operation of the insertion/removal state detection device 41, and outputs the generated synchronization signal to the image pickup device driving unit 32 and the insertion/removal state detection device 41.

More specifically, the controller 38 generates a synchronization signal to align a cycle in which the image pickup device 22b of the image pickup unit 22 outputs the image pickup signal and a cycle in which the encoder 41b of the insertion/removal state detection device 41 outputs the detection signal, to a predetermined cycle (for example, 1/60 seconds), and outputs the generated synchronization signal to the image pickup device driving unit 32 and the insertion/removal state detection device 41.

Figure 4:
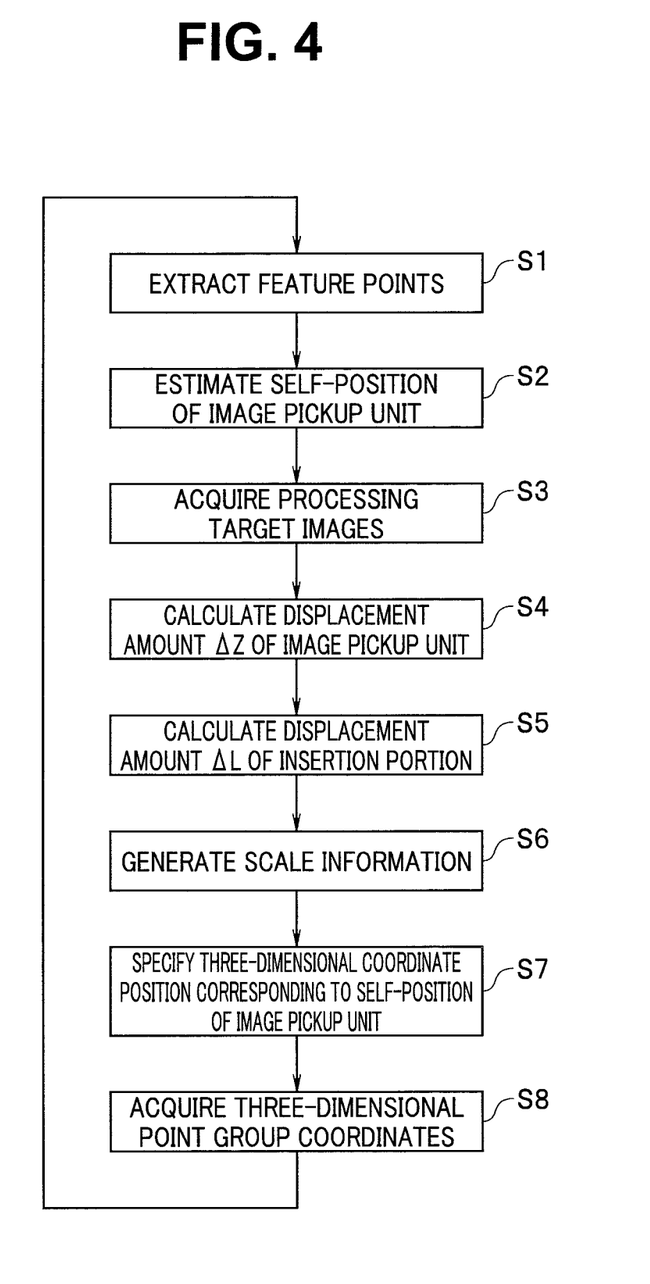
FIG. 4 is a flowchart to explain processing and the like performed by the endoscopic image processing apparatus according to the embodiment.

The controller 38 outputs the above-described synchronization signal during a period when the distal end portion 11 is disposed inside the object and performs processing, for example, as illustrated in FIG. 4 based on the endoscopic image group outputted from the image generation unit 34 and the detection signal outputted from the insertion/removal state detection device 41. The detail of such processing is described below. FIG. 4 is a flowchart to explain the processing and the like performed by the endoscopic image processing apparatus according to the embodiment.

The controller 38 performs the processing to extract a plurality of feature points CP matching in the endoscopic image group outputted from the image generation unit 34 (step S1 of FIG. 4).

More specifically, the controller 38 extracts the plurality of feature points CP matching in the endoscopic image group outputted from the image generation unit 34 by, for example, applying algorithm such as ORB (oriented FAST and rotated BRIEF) to the endoscopic image group.

The controller 38 performs the processing to estimate the self-position of the image pickup unit 22 based on the plurality of feature points CP extracted by the processing in step S1 of FIG. 4 (step S2 of FIG. 4).

More specifically, the controller 38 estimates the self-position of the image pickup unit 22 corresponding to the plurality of feature points CP by, for example, performing processing based on an E matrix (essential matrix) acquired by using a method such as five-point algorithm.

In other words, the controller 38 includes a function as an estimation unit, and estimates the self-position of the image pickup unit 22 based on the endoscopic image group obtained by picking up images of the inside of the object by the endoscope 2.

The controller 38 performs processing to acquire one or more processing target images IG from the endoscopic image group used for extraction of the plurality of feature points CP, based on the plurality of feature points CP extracted by the processing in step S1 of FIG. 4 and an estimation result of the self-position of the image pickup unit 22 obtained by the processing in step S2 of FIG. 4 (step S3 of FIG. 4).

More specifically, the controller 38 acquires one or more processing target images IG based on, for example, the number of feature points CP extracted by the processing in step S1 of FIG. 4 and an elapsed time after the latest estimation result of the self-position of the image pickup unit 22 is acquired by the processing in step S2 of FIG. 4.

The controller 38 performs processing to calculate a displacement amount $\Delta Z$ of the image pickup unit 22 based on the estimation result of the self-position of the image pickup unit 22 obtained by the processing in step S2 of FIG. 4 (step S4 of FIG. 4).

More specifically, the controller 38 performs, as the processing to calculate the displacement amount $\Delta Z$, for example, processing to calculate a distance between the self-position of the image pickup unit 22 obtained as the estimation result at a time point T1 and the self-position of the image pickup unit 22 obtained as the estimation result at a time point T2 after the time point T1.

In other words, the controller 38 includes a function as a first displacement amount calculation unit, and calculates a first displacement amount corresponding to the displacement amount of the image pickup unit 22 based on the estimation result of the self-position of the image pickup unit 22 obtained by the processing in step S2 of FIG. 4.

The controller 38 performs processing to calculate a displacement amount $\Delta L$ of the insertion portion 5 based on the detection signal outputted from the encoder 41$b$ (step S5 of FIG. 4).

More specifically, the controller 38 performs, as the processing to calculate the displacement amount $\Delta L$ of the insertion portion 5, for example, processing to calculate a difference value between a displacement amount $\Delta L1$ of the insertion portion 5 at the time point T1 and a displacement amount $\Delta L2$ of the insertion portion 5 at the time point T2, based on the detection signal outputted from the encoder 41$b$.

Note that, in the present embodiment, the displacement amount of the insertion portion 5 in the longitudinal axis direction is calculated as the displacement amount $\Delta L$. In other words, the controller 38 includes a function as a second displacement amount calculation unit, and calculates a second displacement amount corresponding to the displacement amount of the insertion portion 5 in the longitudinal axis direction based on the detection signal outputted from the insertion/removal state detection device 41.

The controller 38 performs processing to generate scale information SJ by associating the displacement amount $\Delta Z$ calculated by the processing in step S4 of FIG. 4 with the displacement amount $\Delta L$ calculated by the processing in step S5 of FIG. 4 (step S6 of FIG. 4).

In other words, the scale information SJ is generated as information in which a length of the displacement amount $\Delta L$ corresponding to a physical amount measured based on the insertion/removal state of the insertion portion 5 is added to the displacement amount $\Delta Z$ having unknown scale. The controller 38 includes a function as a scale information generation unit, and generates the scale information in which the displacement amount $\Delta Z$ and the displacement amount $\Delta L$ are associated with each other, as information used in the processing to create the three-dimensional shape model of the object.

The controller 38 performs processing to specify a three-dimensional coordinate position of the image pickup unit 22 in a world coordinate system of a three-dimensional space in which the three-dimensional shape model of the object is created, based on the estimation result of the self-position of the image pickup unit 22 obtained by the processing in step S2 of FIG. 4 and the scale information SJ (step S7 of FIG. 4).

The controller 38 performs processing to acquire three-dimensional point group coordinates including the three-dimensional coordinate position of the world coordinate system corresponding to the plurality of feature points CP in the one or more processing target images IG, based on the three-dimensional coordinate position of the image pickup unit 22 obtained by the processing in step S7 of FIG. 4 (step S8 of FIG. 4).

The controller 38 acquires a plurality of three-dimensional point group coordinates by, for example, repeating the series of processing of FIG. 4 a plurality of times. Further, the controller 38 creates the three-dimensional shape model of the object by performing densification processing to integrate the plurality of acquired three-dimensional point group coordinates into one coordinate.

As described above, according to the present embodiment, the three-dimensional coordinate position of the image pickup unit 22 is specified based on the scale information SJ representing a correspondence relationship between the displacement amount $\Delta Z$ and the displacement amount $\Delta L$, and the three-dimensional point group coordinates are acquired based on the specified three-dimensional coordinate position of the image pickup unit 22. Therefore, it is possible to create the three-dimensional shape model of the object with high accuracy by using the acquired three-dimensional point group coordinates. Thus, according to the present embodiment, it is possible to improve inspection efficiency in inspection of an object having unknown scale in a real space.

According to the present embodiment, it is sufficient to perform the processing in step S6 of FIG. 4 one or more times while the insertion portion 5 is inserted into the object. In other words, according to the present embodiment, it is sufficient for the controller 38 to generate at least one piece of scale information SJ during repetition of the processing in FIG. 4.

According to the present embodiment, for example, in a case where the controller 38 performs control to direct the distal end portion 11 to the direction intersecting the longitudinal axis direction of the insertion portion 5 by bending the bending portion 12, namely, in a case where the displacement amount $\Delta L$ is calculated in a state where the visual field direction of the image pickup unit 22 and the displacement direction (insertion direction or removal direction) of the insertion portion 5 are not coincident with each other, the processing relating to the scale information SJ corresponding to the processing in steps S4 to S7 of FIG. 4 may not be performed.

Note that the processing relating to the scale information SJ includes the processing to generate the scale information SJ and the processing using the scale information SJ. Therefore, in a case where the processing relating to the scale information SJ is not performed, the controller 38 performs processing to acquire the three-dimensional point group coordinates including the three-dimensional coordinate position of the world coordinate system corresponding to the plurality of feature points CP in the one or more processing target images IG, based on the estimation result of the self-position of the image pickup unit 22 obtained by the processing in step S2 of FIG. 4, in place of the processing in step S8 of FIG. 4.

The present embodiment is applicable not only to the endoscope system 1 including the endoscope 2 provided with the soft (flexible) insertion portion 5 but also to other endoscope systems each including an endoscope provided with a rigid (inflexible) insertion portion in substantially the same manner.

Figure 5:
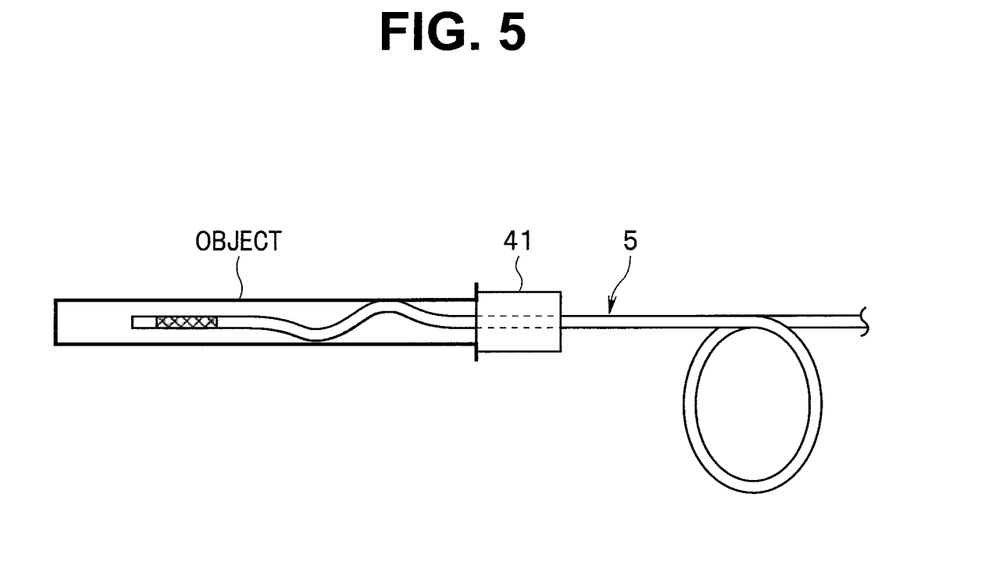
FIG. 5 is a diagram illustrating an example of a state where deflection occurs in the insertion portion inserted into an object.

In the endoscope 2 provided with the soft insertion portion 5, for example deflection as illustrated in FIG. 5 may occur due to the insertion operation by the user. In a state where the deflection as illustrated in FIG. 5 occurs, accuracy of the scale information SJ may not be secured due to separation of an actual displacement amount ΔZr of the distal end portion 11 (image pickup unit 22) and the displacement amount ΔL of the insertion portion 5 calculated based on the detection signal outputted from the insertion/removal state detection device 41. FIG. 5 is a diagram illustrating an example of a state where deflection occurs in the insertion portion inserted into the object.

Figure 6:
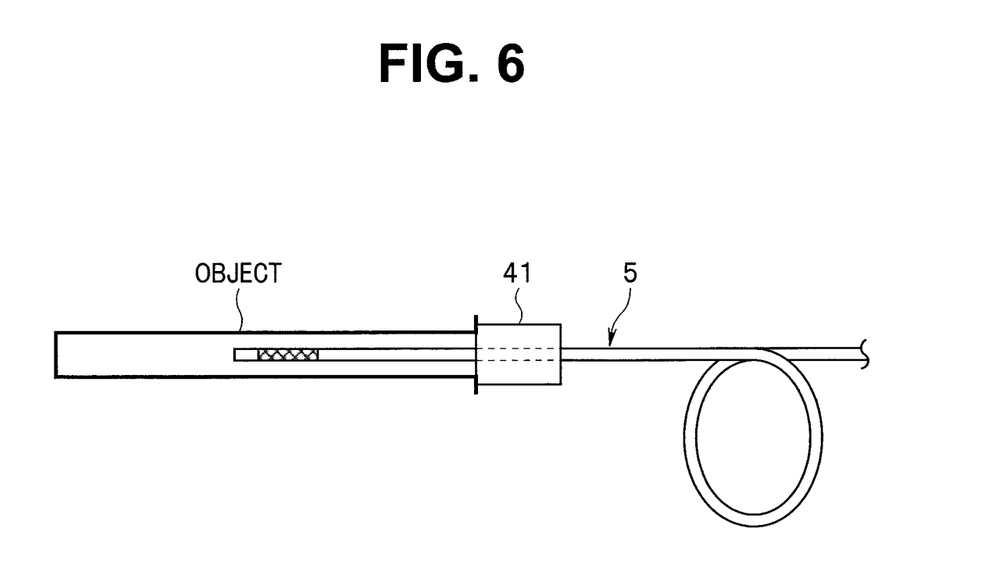
FIG. 6 is a diagram illustrating an example of a state where no deflection occurs in the insertion portion inserted into the object.

Therefore, in a case where the present embodiment is applied to the endoscope system 1 including the endoscope 2, the processing relating to the scale information SJ is desirably performed while no deflection occurs in the insertion portion 5, for example, as illustrated in FIG. 6. Further, during the removal operation of the insertion portion 5 performed by the user, the deflection as illustrated in FIG. 5 may be eliminated by displacement of the insertion portion 5 in the removal direction. Therefore, the displacement amount ΔZr and the displacement amount ΔL are easily coincident with each other. FIG. 6 is a diagram illustrating an example of a state where no deflection occurs in the insertion portion inserted into the object.

In other words, in the case where the present embodiment is applied to the endoscope system 1 including the endoscope 2, for example, the controller 38 detects the displacement direction of the insertion portion 5 based on the detection signal outputted from the insertion/removal state detection device 41. In a case where the detected displacement direction of the insertion portion 5 is the removal direction, the controller 38 performs the processing relating to the scale information SJ, whereas in a case where the detected displacement direction of the insertion portion 5 is the insertion direction, the controller 38 does not perform the processing relating to the scale information SJ. Such processing makes it possible to secure accuracy of the scale information SJ.

According to the present embodiment, the controller 38 may perform processing to further improve accuracy of the scale information SJ generated in the case where the displacement direction of the insertion portion 5 is the removal direction. Such processing according to a modification of the present embodiment is described below. Note that, in the following, specific descriptions about portions to which the above-described operation and the like are applicable are appropriately omitted.

After the user turns on the units of the endoscope system 1, the user brings the distal end portion 11 to the deepest site of the object by performing the insertion operation to insert the insertion portion 5 into the object. Further, after the user brings the distal end portion 11 to the deepest site of the object, the user performs the removal operation to remove the insertion portion 5 from the inside of the object.

For example, in a case where the displacement direction of the insertion portion 5 detected based on the detection signal outputted from the insertion/removal state detection device 41 is the removal direction, the controller 38 calculates a displacement speed VZ of the image pickup unit 22 by dividing the displacement amount ΔZ obtained by the processing in step S4 of FIG. 4 by a predetermined unit time TP. Further, for example, in the case where the displacement direction of the insertion portion 5 detected based on the detection signal outputted from the insertion/removal state detection device 41 is the removal direction, the controller 38 calculates a displacement speed VL of the insertion portion 5 by dividing the displacement amount ΔL obtained by the processing in step S5 of FIG. 4 by the predetermined unit time TP. Further, the controller 38 determines whether to perform the processing (generation of scale information SJ) in step S6 of FIG. 4 based on correlation between variation of the displacement speed VZ in a predetermined time width TW and variation of the displacement speed VL in the predetermined time width TW.

Figure 7A:
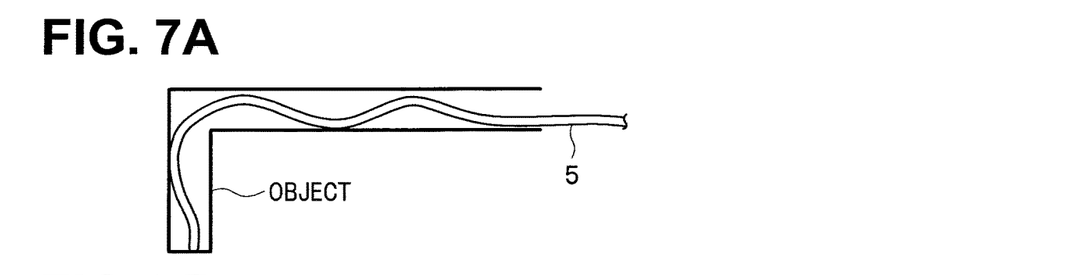
FIG. 7A is a diagram illustrating an example of the state where deflection occurs in the insertion portion inserted into the object.
Figure 7B:
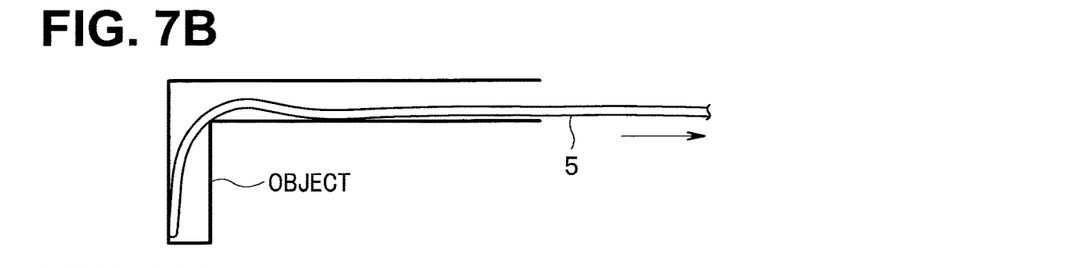
FIG. 7B is a diagram illustrating a state where the deflection occurring in the insertion portion inserted into the object is eliminated by removal operation.
Figure 7C:
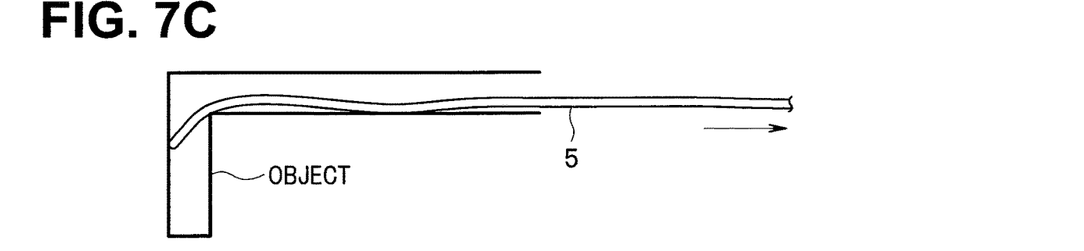
FIG. 7C is a diagram illustrating the state where the deflection occurring in the insertion portion inserted into the object is eliminated by the removal operation.
Figure 7D:
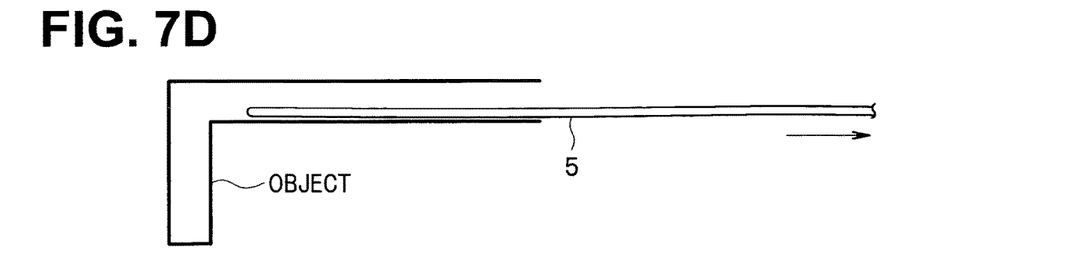
FIG. 7D is a diagram illustrating an example of a state where the deflection occurring in the insertion portion inserted into the object is completely eliminated by the removal operation.
Figure 7E:
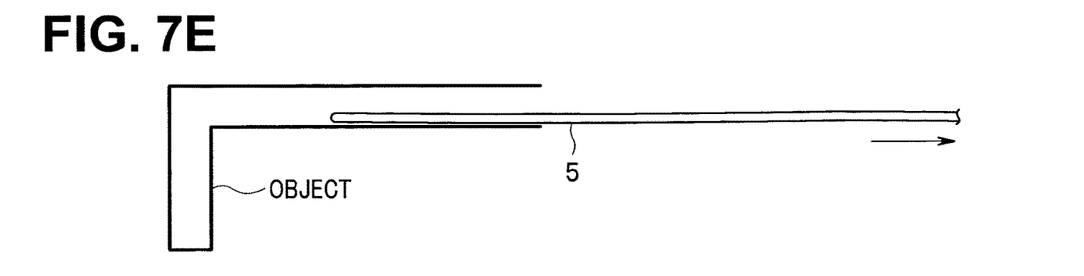
FIG. 7E is a diagram illustrating an example of the state where the deflection occurring in the insertion portion inserted into the object is completely eliminated by the removal operation.

In a state where the distal end portion 11 has reached the deepest site of the object by the insertion operation of the user, for example, deflection as illustrated in FIG. 7A may occur. Therefore, in a case where deflection occurs in the insertion portion 5, a state where the displacement amount ΔZr and the displacement amount ΔL are easily separated is continued during a period after start of removal of the insertion portion 5 until the deflection of the insertion portion 5 is completely eliminated, for example, as illustrated in FIG. 7B and FIG. 7C. Further, during a period after the deflection of the insertion portion 5 is completely eliminated by the removal operation of the insertion portion 5 by the user, for example, as illustrated in FIG. 7D and FIG. 7E, the displacement amount ΔZr and the displacement amount ΔL are hardly separated. Note that, in FIG. 7A to FIG. 7E, illustration of the insertion/removal state detection device 41 is omitted. FIG. 7A is a diagram illustrating an example of the state where deflection occurs in the insertion portion inserted into the object. FIG. 7B and FIG. 7C are diagrams each illustrating a state where the deflection occurring in the insertion portion inserted into the object is eliminated by the removal operation. FIG. 7D and FIG. 7E are diagrams each illustrating an example of a state where the deflection occurring in the insertion portion inserted into the object is completely eliminated by the removal operation.

Figure 8A:
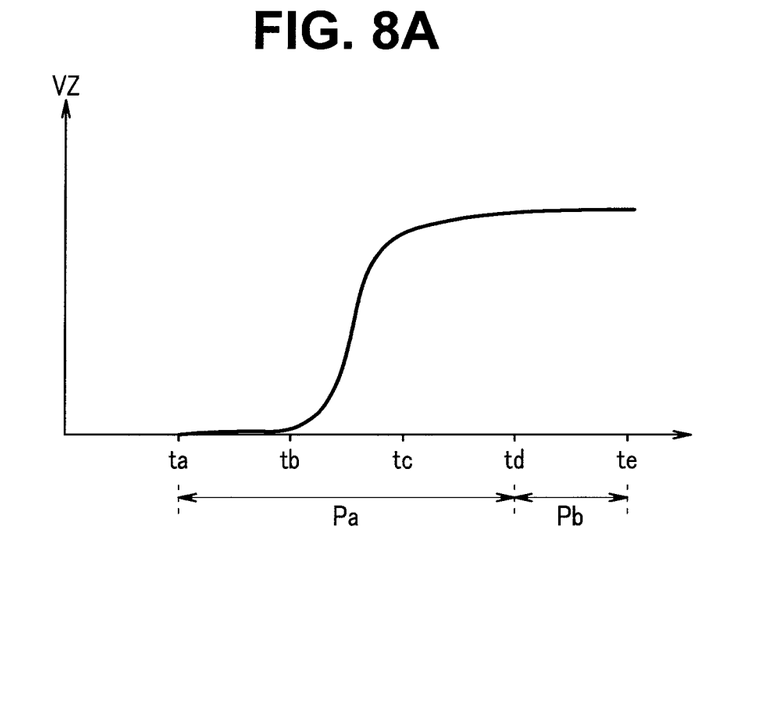
FIG. 8A is a diagram illustrating an example of temporal variation of a displacement speed VZ.
Figure 8B:
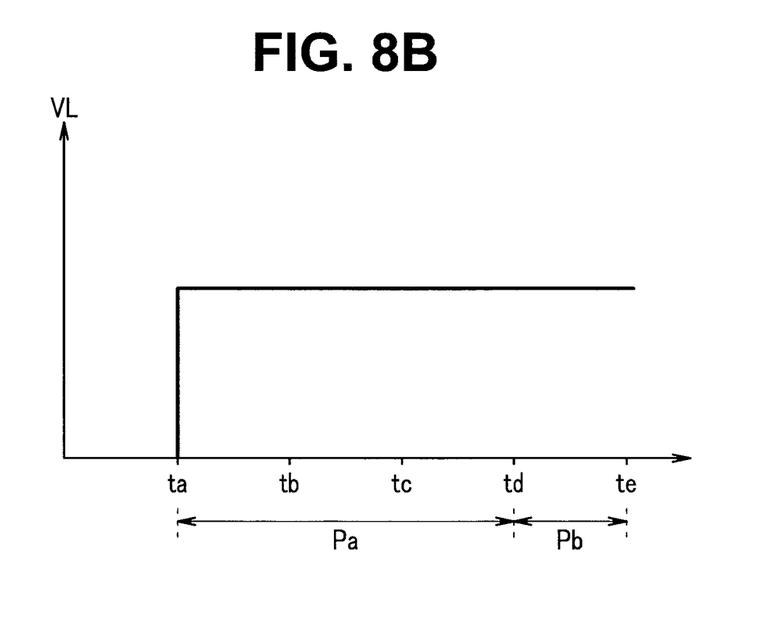
FIG. 8B is a diagram illustrating an example of temporal variation of a displacement speed VL.

In a case where the state of FIG. 7A occurs at a time point ta, the state of FIG. 7B occurs at a time point tb, the state of FIG. 7C occurs at a time point tc, the state of FIG. 7D occurs at a time point td, and the state of FIG. 7E occurs at a time point te, temporal variation of the displacement speed VZ can be illustrated as in FIG. 8A, and temporal variation of the displacement speed VL can be illustrated as in FIG. 8B. FIG. 8A is a diagram illustrating an example of the temporal variation of the displacement speed VZ. FIG. 8B is a diagram illustrating an example of the temporal variation of the displacement speed VL.

The controller 38 does not perform the processing in step S6 of FIG. 4 during a period when correlation between variation of the displacement speed VZ in the predetermined time width TW and variation of the displacement speed VL in the predetermined time width TW is low, namely, during a period Pa from the time point ta to the time point td. Further, the controller 38 performs the processing in step S6 of FIG. 4 during a period when the correlation between the variation of the displacement speed VZ in the predetermined time width TW and the variation of the displacement speed VL in the predetermined time width TW is high, namely, during a period Pb immediately after the time point td to the time point te.

Figure 9A:
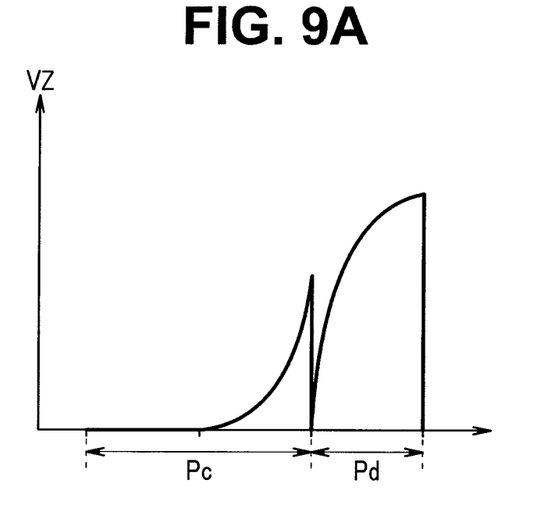
FIG. 9A is a diagram illustrating an example of the temporal variation of the displacement speed VZ.
Figure 9B:
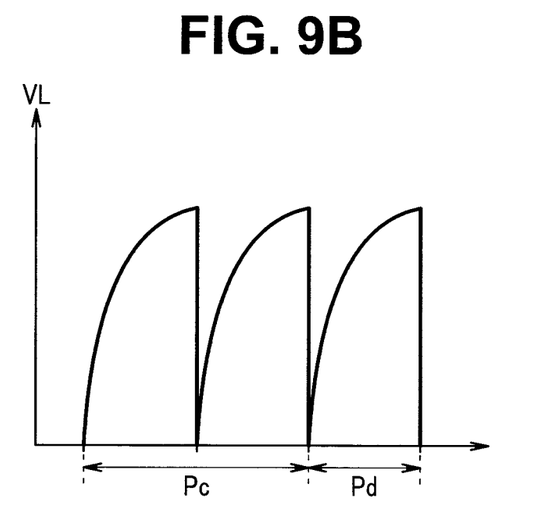
FIG. 9B is a diagram illustrating an example of the temporal variation of the displacement speed VL.

The processing of the controller 38 according to the present modification is applicable not only to the case as illustrated in FIGS. 8A and 8B but also to, for example, a case as illustrated in FIG. 9A and FIG. 9B in substantially the same manner. FIG. 9A is a diagram illustrating an example of the temporal variation of the displacement speed VZ. FIG. 9B is a diagram illustrating an example of the temporal variation of the displacement speed VL.

More specifically, the controller 38 does not perform the processing in step S6 of FIG. 4 during a period Pc corresponding to the period when the correlation between the variation of the displacement speed VZ in the predetermined time width TW and the variation of the displacement speed VL in the predetermined time width TW is low. Further, the controller 38 performs the processing in step S6 of FIG. 4 during a period Pd corresponding to the period when the correlation between the variation of the displacement speed VZ in the predetermined time width TW and the variation of the displacement speed VL in the predetermined time width TW is high.

As described above, by the processing of the controller 38 according to the present modification, the scale information SJ is generated during the period when the displacement amount ΔZr and the displacement amount ΔL are hardly separated in the period when the insertion portion 5 is removed from the inside of the object. Therefore, the processing of the controller 38 according to the present modification makes it possible to further improve accuracy of the scale information SJ generated in the case where the displacement direction of the insertion portion 5 is the removal direction.

The present invention is not limited to the above-described embodiment, and various modifications and applications can be made without departing from the gist of the present invention as a matter of course.

What is claimed is:

1. An endoscopic image processing apparatus comprising: one or more processors configured to:
    acquire an endoscopic image group obtained by causing an image pickup device provided at a distal end portion of an elongated insertion portion to pick up images of an inside of an object;
    estimate a self-position of the image pickup device based on the endoscopic image group;
    calculate a first displacement amount corresponding to a displacement amount of the image pickup device based on an estimation result of the self-position of the image pickup device obtained by the estimation;
    acquire, from an insertion/removal state detection device that detects an insertion/removal state with respect to the object of the insertion portion inserted into the object, a detection signal indicating the insertion/removal state;
    calculate a second displacement amount corresponding to a displacement amount in a direction parallel to a longitudinal axis direction of the insertion portion, based on the detection signal; and
    generate scale information in which the first displacement amount and the second displacement amount are associated with each other.

2. The endoscopic image processing apparatus according to claim 1,
    wherein the one or more processors are configured to:
        detect a displacement direction of the insertion portion based on the detection signal;
        in a case where the detected displacement direction of the insertion portion is a removal direction, perform processing to generate the scale information; and
        in a case where the detected displacement direction of the insertion portion is an insertion direction, not perform the processing to generate the scale information.

3. The endoscopic image processing apparatus according to claim 1,
    wherein the one or more processors are configured to:
        calculate a first displacement speed corresponding to a displacement speed of the image pickup device based on the first displacement amount;
        calculate a second displacement speed corresponding to a displacement speed of the insertion portion based on the second displacement amount; and
        determine whether to perform processing to generate the scale information, based on correlation between variation of the first displacement speed in a predetermined time width and variation of the second displacement speed in the predetermined time width.

4. The endoscopic image processing apparatus according to claim 1,
    wherein the one or more processors is configured to, in a case where control to direct the distal end portion to a direction intersecting the longitudinal axis direction of the insertion portion is performed, not perform processing to generate the scale information.

5. The endoscopic image processing apparatus according to claim 1,
    wherein the insertion/removal state detection device is disposed at a position where a relative position to the object into which the insertion portion is inserted is not changed.

6. The endoscopic image processing apparatus according to claim 5,
    wherein the insertion/removal state detection device is fixed at a predetermined position near an insertion port for insertion of the insertion portion into the object.

7. The endoscopic image processing apparatus according to claim 1,
    wherein the one or more processors are configured to generate the scale information in which the first displacement amount having unknown scale and the second displacement amount are associated with each other, as the information used for the processing relating to creation of a three-dimensional shape model of the object.

8. An endoscope system, comprising:
    an endoscope comprising an insertion portion and an image pickup device provided at a distal end portion of the insertion portion;
    an insertion/removal state detection device configured to detect an insertion/removal state of the insertion portion inserted into an object and to output a detection signal; and
    one or more processors configured to:
        acquire an endoscopic image group obtained by causing the image pickup device to pick up images of an inside of the object;
        estimate a self-position of the image pickup device based on the endoscopic image group;

calculate a first displacement amount corresponding to a displacement amount of the image pickup device based on an estimation result of the self-position of the image pickup device obtained by the estimation;

calculate a second displacement amount corresponding to a displacement amount in a direction parallel to a longitudinal axis direction of the insertion portion, based on the detection signal outputted from the insertion/removal state detection device; and generate scale information in which the first displacement amount and the second displacement amount are associated with each other.

9. A method comprising:

acquiring an endoscopic image group obtained by causing an image pickup device provided at a distal end portion of an elongated insertion portion to pick up images of an inside of an object;

estimating a self-position of the image pickup device based on the endoscopic image group;

calculating a first displacement amount corresponding to a displacement amount of the image pickup device based on an estimation result of the self-position of the image pickup device obtained by the estimation;

acquiring, from an insertion/removal state detection device that detects an insertion/removal state with respect to the object of the insertion portion inserted into the object, a detection signal indicating the insertion/removal state;

calculating a second displacement amount corresponding to a displacement amount in a direction parallel to a longitudinal axis direction of the insertion portion, based on the detection signal; and generating scale information in which the first displacement amount and the second displacement amount are associated with each other.

10. A non-transitory computer-readable storage medium storing instructions that cause a computer to at least perform:

acquiring an endoscopic image group obtained by causing an image pickup device provided at a distal end portion of an elongated insertion portion to pick up images of an inside of an object;

estimating a self-position of the image pickup device based on the endoscopic image group;

calculating a first displacement amount corresponding to a displacement amount of the image pickup device based on an estimation result of the self-position of the image pickup device obtained by the estimation;

acquiring, from an insertion/removal state detection device that detects an insertion/removal state with respect to the object of the insertion portion inserted into the object, a detection signal indicating the insertion/removal state;

calculating a second displacement amount corresponding to a displacement amount in a direction parallel to a longitudinal axis direction of the insertion portion, based on the detection signal; and generating scale information in which the first displacement amount and the second displacement amount are associated with each other.

11. The endoscopic image processing apparatus according to claim 1,
wherein the one or more processors are configured to:
extract a plurality of matching feature points in the endoscopic image group; and
estimate the self-position of the image pickup device based on the plurality of matching feature points.

12. The endoscopic image processing apparatus according to claim 1,
wherein the one or more processors are configured to specify a three-dimensional coordinate position of the image pickup device in a world coordinate system of a three-dimensional space in which a three-dimensional shape model of the object is created, based on the estimation result of the self-position of the image pickup device.

13. The endoscopic image processing apparatus according to claim 12,
wherein the one or more processors are configured to specify the three-dimensional coordinate position of the image pickup device based on the estimation result of the self-position of the image pickup device and the scale information.

14. The endoscopic image processing apparatus according to claim 12,
wherein the one or more processors are configured to acquire three-dimensional point group coordinates including the three-dimensional coordinate position of the world coordinate system corresponding to the plurality of feature points based on the three-dimensional coordinate position.

15. The endoscopic image processing apparatus according to claim 12,
wherein the one or more processors are configured to create the three-dimensional shape model of the object based on at least one of the three-dimensional point group coordinates.

16. The endoscopic image processing apparatus according to claim 1,
wherein the first displacement amount is a displacement amount between a first estimation result of the self-position of the image pickup device acquired at a first timing and a second estimation result of the self-position of the image pickup device at a second timing, the first timing being different from the second timing.

17. The endoscopic image processing apparatus according to claim 1,
wherein the insertion/removal detection device includes a roller, and the detection signal corresponds to a rotation amount and a rotation direction of the roller.

18. The endoscopic image processing apparatus according to claim 1,
wherein the one or more processors are configured to generate a synchronization signal to synchronize a cycle in which the image pickup device outputs an image pickup signal with a cycle in which the insertion/removal detection device outputs the detection signal.

* * * * *

UNITED STATES PATENT AND TRADEMARK OFFICE
CERTIFICATE OF CORRECTION

| | | |
|---|---|---|
| PATENT NO. | : 12,067,672 B2 | Page 1 of 1 |
| APPLICATION NO. | : 17/513353 | |
| DATED | : August 20, 2024 | |
| INVENTOR(S) | : Hideaki Takahashi | |

It is certified that error appears in the above-identified patent and that said Letters Patent is hereby corrected as shown below:

On the Title Page

Item (71) should read:
(71) Applicant: EVIDENT CORPORATION, Nagano (JP)

Signed and Sealed this
Thirty-first Day of December, 2024

Derrick Brent
*Acting Director of the United States Patent and Trademark Office*